United States Patent [19]
Shimada et al.

[11] Patent Number: 6,107,064
[45] Date of Patent: *Aug. 22, 2000

[54] PROCESS FOR PRODUCING XANTHINE DERIVATIVES WITH BACTERIA AND FUNGI

[75] Inventors: Junichi Shimada, Sunto-gun; Tamotsu Eguchi, Machida; Kenichi Mochida, Hiratsuka; Akira Horiguchi, Mishima, all of Japan; Tohru Yasuzawa, Cary, N.C.; Hideaki Kusaka; Hiromi Nonaka, both of Sunto-gun, Japan; Fumio Suzuki, Mishima, Japan

[73] Assignee: Kyowa Hakko Kogyo Co., Ltd., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/581,533
[22] PCT Filed: May 16, 1995
[86] PCT No.: PCT/JP95/00929
§ 371 Date: Jan. 17, 1996
§ 102(e) Date: Jan. 17, 1996
[87] PCT Pub. No.: WO95/31460
PCT Pub. Date: Nov. 23, 1995

[30] Foreign Application Priority Data

May 17, 1994 [JP] Japan ................................. 6/102778
Sep. 6, 1994 [JP] Japan ................................. 6/211637

[51] Int. Cl.[7] .................................................. C12P 17/16
[52] U.S. Cl. ........................................... 435/119; 435/118
[58] Field of Search ..................... 435/119, 911, 435/118

[56] References Cited

U.S. PATENT DOCUMENTS

| | | | |
|---|---|---|---|
| 3,649,452 | 3/1972 | Herr | 435/119 |
| 3,706,801 | 12/1972 | Herr | 435/119 |
| 5,290,782 | 3/1994 | Suzuki et al. | 514/263 |
| 5,338,743 | 8/1994 | Shizokawa et al. | 514/300 |

FOREIGN PATENT DOCUMENTS

| | | |
|---|---|---|
| 0541120 | 5/1993 | European Pat. Off. . |
| 0560354 | 9/1993 | European Pat. Off. . |
| 619316 | 10/1994 | European Pat. Off. . |
| 270222 | 9/1992 | Japan . |

OTHER PUBLICATIONS

ATCC Catalogue of Fungi, 1991, p. 74.
Kieslich, K., Microbial Transformations of Non–Steroid Compounds, 1976, pp. 410–417.
Chemical Abstracts, vol. 118, No. 25, Jun. 21, 1993, Abstract No. 254632t.

*Primary Examiner*—Irene Marx
*Attorney, Agent, or Firm*—Fitzpatrick Cella Harper & Scinto

[57] ABSTRACT

The present invention relates to a process for producing a xanthine derivative represented by formula (II), comprising converting a xanthine derivative represented by formula (I) {hereinafter, referred to as Compound (I)}:

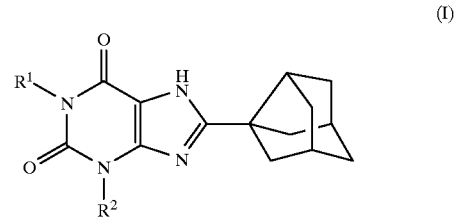

(I)

(wherein $R^1$ and $R^2$ independently represent hydrogen, or hydroxy-substituted, oxo-substituted, or unsubstituted lower alkyl) into a xanthine derivative represented by formula (II) {hereinafter, referred to as Compound (II)}:

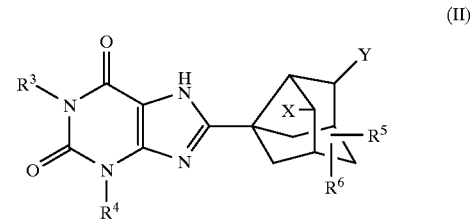

(II)

(wherein $R^3$ and $R^4$ independently represent hydrogen, or hydroxy-substituted, oxo-substituted, or unsubstituted lower alkyl; $R^5$ and $R^6$ independently represent hydrogen, hydroxy, or oxo; with the proviso that $R^5$ and $R^6$ are both hydrogen, at least one of $R^3$ and $R^4$ is hydroxy-substituted or oxo-substituted lower alkyl; and X and Y both represent hydrogen or are combined with each other to form a single bond) in the presence of an enzyme source for catalyzing hydroxylation or carbonylation of Compound (I) into Compound (II), and collecting the produced Compound (II).

5 Claims, No Drawings

PROCESS FOR PRODUCING XANTHINE DERIVATIVES WITH BACTERIA AND FUNGI

TECHNICAL FIELD

The present invention relates to a process for producing a xanthine derivative having adenosine $A_1$ receptor antagonizing activity, and exhibiting diuretic effect, renal-protecting effect, bronchodilatory effect, cerebral function improving effect, etc.

BACKGROUND ART

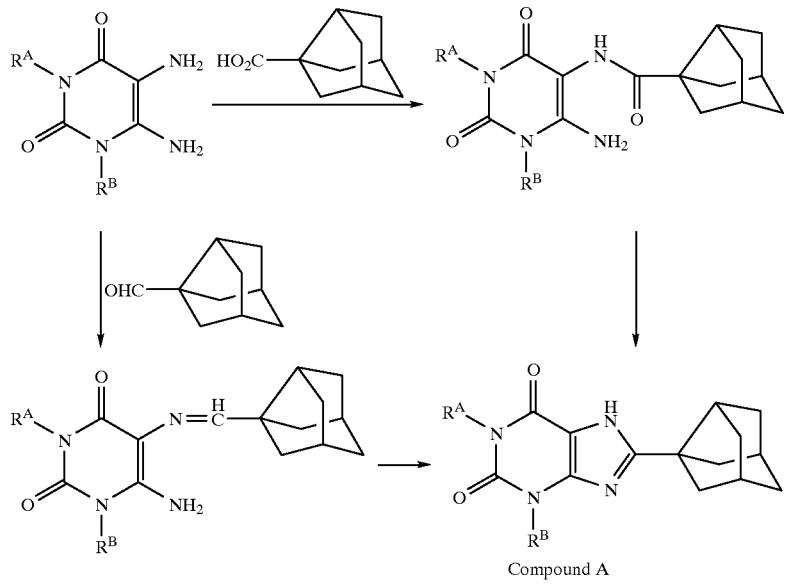

Compound A (In the formulae, $R^A$ and $R^B$ are lower alkyl.)

A process for synthesizing a xanthine derivative (Compound A) is known in which uracil and a carboxylic acid or aldehyde are used as starting materials, as shown by the above formulae (Japanese Published Unexamined Patent Application No.173889/91). It is known that Compound A has activity of selectively antagonizing adenosine $A_1$ receptor and shows diuretic effect, renal-protecting effect, bronchodilatory effect, etc. (Japanese Published Unexamined Patent Application No.173889/91), and cerebral function improving effect (Japanese Published Unexamined Patent Application No.270222/92).

It is also known that a xanthine derivative (Compound B) represented by the formula Compound B

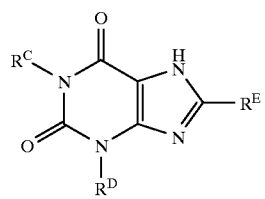

(wherein $R^C$ and $R^D$ are hydroxy-substituted or unsubstituted lower alkyl, and $R^E$ is substituted or unsubstituted tricycloalkyl of $C_7$–$C_{12}$) shows anti-ulcerative effect and the like (Japanese Published Unexamined Patent Application No.58913/93), but no specific examples of the hydroxy-substituted compounds or no methods of producing such compounds are disclosed in the publication.

Disclosure of the Invention

The present invention relates to a process for producing a xanthine derivative represented by formula (II), comprising converting a xanthine derivative represented by formula (I) {hereinafter, referred to as Compound (I) and this applies to the compounds of other formula numbers}:

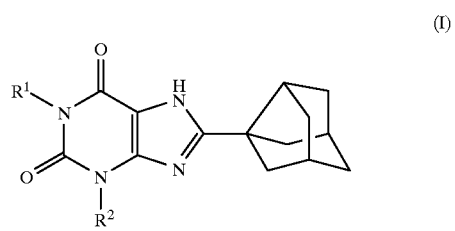

(wherein $R^1$ and $R^2$ independently represent hydrogen, or hydroxy-substituted, oxo-substituted, or unsubstituted lower alkyl) into a xanthine derivative represented by formula (II):

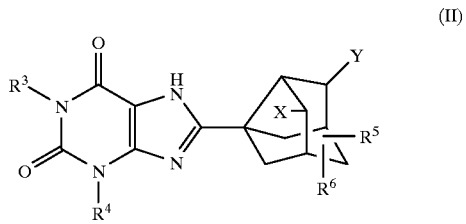

(wherein $R^3$ and $R^4$ independently represent hydrogen, or hydroxy-substituted, oxo-substituted, or unsubstituted lower alkyl; $R^5$ and $R^6$ independently represent hydrogen, hydroxy, or oxo; with the proviso that $R^5$ and $R^6$ are both hydrogen, at least one of $R^3$ and $R^4$ is hydroxy-substituted or oxo-substituted lower alkyl; and X and Y both represent hydrogen or are combined with each other to form a single bond) in the presence of an enzyme source for catalyzing hydroxylation or carbonylation of Compound (I) into Compound (II), and collecting the produced Compound (II).

The present invention also provides a process for producing Compound (II), comprising converting a uracil derivative represented by formula (III):

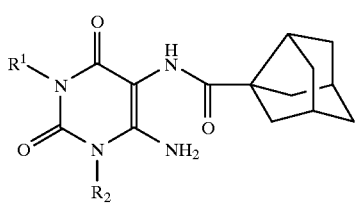

(III)

(wherein $R^1$ and $R^2$ have the same meanings as defined above) into a uracil derivative represented by formula (IV):

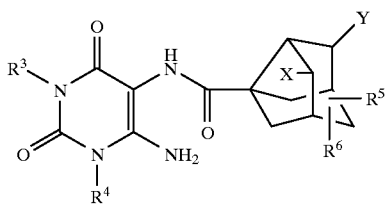

(IV)

(wherein $R^3$, $R^4$, $R^5$, $R^6$, X, and Y have the same meanings as defined above) in the presence of an enzyme source for catalyzing hydroxylation or carbonylation of Compound (III) into Compound (IV), and then closing a ring of Compound (IV) by dehydration.

The present invention further provides a xanthine derivative represented by formula (IIa):

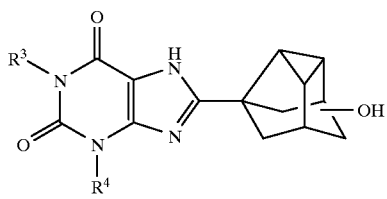

(IIa)

(wherein $R^3$ and $R^4$ have the same meanings as defined above), or a pharmaceutically acceptable salt thereof.

In the definitions of Compound (I), Compound (II), Compound (III), Compound (IV), and Compound (IIa), the lower alkyl means a straight-chain or branched alkyl group having 1 to 6 carbon atoms such as methyl, ethyl, propyl, isoproyl, butyl, isobutyl, sec-butyl, tert-butyl, pentyl, and hexyl.

The enzyme source used in the present invention is not limited, and any enzymes, enzyme complexes, and substances containing them can be used as the enzyme source, so long as they have the activity of catalyzing a reaction for producing Compound (II) or Compound (IV) by regiospecific or stereospecific hydroxylation or carbonylation of Compound (I) or Compound (II).

Cytochrome P450 enzyme complexes, hydroxylase, etc. can be used as enzymes or enzyme complexes. These enzymes or enzyme complexes are produced by microorganisms, animal tissues, or plant tissues. Examples of the substances containing enzymes or enzyme complexes are bacteria of microorganisms having the ability to produce the above enzymes or enzyme complexes, culture solutions containing the bacteria, and treatment products of the bacteria.

Preferable examples of such microorganisms are microorganisms belonging to the genus Absidia, Bacillus, Beauveria, Cunninghamella, Gongronella, or Mucor. Further, specific examples of such microorganisms are *Absidia ramosa* FERM BP-4605, *Bacillus megaterium* FERM BP-4606, *Beauveria bassiana* IFO-4848, *Beauveria bassiana* FERM BP-4607, *Cunninghamella echinulata* var. *elegans* IFO-6334, *Gongronella butleri* OUT-1001, and *Mucor hiemalis* FERM P-5708.

The mycological properties of *Absidia ramosa, Bacillus megaterium,* and *Beauveria bassiana* are described in detail in Mucorales (J. Cramer), 103–104 (1969) (H. Zycha, R. Siepmann, and G. Linnemann), Bergey's Manual of Systematic Bacteriology, 2, 1133 (1986), and the genera Beauveria, Isaria, Tritirachium and Acrodontium gen.nov., 4–10 (G. S. De Hoog) in Studies in Mycology (Baarn), No. 1 (1972), respectively.

As treatment products of the bacteria, dried bacteria, freeze-dried bacteria, surfactant and/or organic solvent addition products, lytic enzyme-treated bacteria, ultrasonics-crashed bacteria, immobilized bacteria, and samples extracted from bacteria can be used. Enzymes which are obtained by extraction from the bacteria and which have the activity to catalyze hydroxylation or carbonylation of Compound (I) or Compound (III) into Compound (II) or Compound (IV), purified samples thereof, and their immobilized enzymes can also be used.

For the culturing of the above microorganisms, the medium appropriately containing an organic or inorganic carbon source, a nitrogen source, vitamin, minerals, and the like which can generally be assimilated by the bacteria may be used. Further, Compound (I), Compound (III), 1-adamantanamine, 2-adamantanamine, N-(1-adamantyl) urea, barbituric acid, etc. can be added as an enzyme-inducting agent to the medium in an amount of 0.01 to 0.5 wt %.

Any carbon sources may be used, so long as they can be assimilated by microorganisms, and examples of such carbon sources are glucose, fructose, sucrose, treacle, carbohydrates such as starch and starch hydrolysate, organic acid such as acetic acid and propionic acid, and alcohols such as ethanol and propanol.

As the nitrogen sources, ammonia; ammonium salts of various inorganic acids or organic acids such as ammonium chloride, ammonium sulfate, ammonium acetate and ammonium phosphate; other compounds containing nitrogen; peptone; meat extract; yeast extract; corn steep liquor; casein hydrolysate; soybean meal and soybean meal hydrolysate; various fermenting bacteria and digests thereof, etc. may be used.

The pharmaceutically acceptable salts of Compound (IIa) include pharmaceutically acceptable acid addition salts, metal salts, ammonium salts, organic amine addition salts, and amino acid addition salts.

Examples of the pharmaceutically acceptable acid addition salts of Compound (IIa) are inorganic acid addition salts such as hydrochloride, sulfate and phosphate, and organic acid addition salts such as acetate, maleate, fumalate, tartrate and citrate. Examples of the pharmaceutically acceptable metal salts are alkali metal salts such as sodium salt and potassium salt, alkaline earth metal salts such as magnesium salt and calcium salt, aluminium salts, and zinc salts. Examples of the pharmaceutically acceptable ammonium salts are ammonium and tetramethyl ammonium. Examples of the pharmaceutically acceptable organic amine addition salts are salts with morpholine and piperidine. Examples of the pharmaceutically acceptable amino acid addition salts are salts with lysine, glycine, and phenylalanine.

The present invention are described in detail below.
Preparation Process 1:

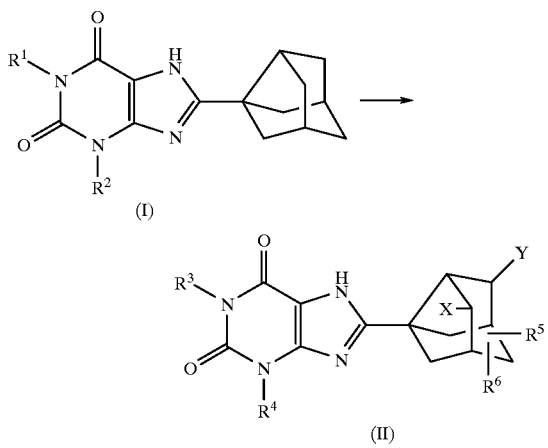

(In the formulae, $R^1$, $R^2$, $R^3$, $R^4$, $R^5$, $R^6$, X, and Y have the same meanings as defined above.)

Compound (II) can be obtained by hydroxylizing or carbonylyzing Compound (I) obtained by a known method (Japanese Published Unexamined Patent Application No.173889/91) in a regiospecific or stereospecific manner in an aqueous medium or an organic solvent in the presence of an enzyme source having the ability to catalyze hydroxylation or carbonylation of Compound (I) into Compound (II).
Method A:

Compound (II) can be obtained by adding Compound (I) to a medium for growing microorganisms having the ability to produce an enzyme or an enzyme complex which can hydoxylyze or carbonylyze a compound in a regiospecific or stereospecific manner, and stirring or shaking with growth of the microorganisms. Compound (I), which serves as a substrate, is used in an amount of 0.01 to 5 wt % based on the medium. At this time, a surfactant such as Bridge 35 or span may be added thereto for improving the dispersibility of Compound (I) serving as the substrate. Further, if necessary, sodium hydroxide, hydrochloric acid, etc. may be added thereto for maintaining the optimum pH of the medium. The preferable pH value is generally 4 to 9. The reaction temperature is 20 to 40° C., preferably 25 to 35° C. Although the reaction time varies depending upon the culture temperature, the substrate concentration, the type of the microorganisms, etc., the reaction is generally completed in 1 to 10 days.

On the other hand, when the reaction is carried out by bringing bacteria into contact with the substrate after culturing, a bacterial suspension obtained by centrifugation after culturing or treatment products of the bacteria can be used. The concentration of Compound (I) serving as the substrate in the reaction solution is generally 0.01 to 5 wt %. The method of addition may be either by batch addition or by division addition. At this time, a surfactant such as Bridge 35 and span, or an organic solvent such as dimethyl sulfoxide, acetonitrile, and ethanol may be added to the medium for improving the dispersibility of Compound (I) serving as the substrate. The reaction temperature is generally 20 to 40° C. The pH value is generally 4 to 9. However, the optimum pH value varies depending upon the type of the bacteria used. Although the reaction time varies depending upon the bacteria, the reaction is generally completed in 3 to 10 days when it is carried out at 30° C.

Conventional separation methods such as column chromatography using an ion-exchange resin, etc., high performance liquid chromatography, and crystallization can be used as the method of recovering Compound (II) from an aqueous medium or an organic solvent.
Method B:

Compound (II) can be obtained by suspending hepatocyte microsome obtained by a known method [Tetsuya Kamataki et al., Applied Pharmacokinetics—Theory and Experiments—, p. 325, edited by Manabu Hanano et al., Soft Science Co., Tokyo (1985)] in a neutral phosphate buffer, adding dihydroxynicotinamide adenine dinucleotide phosphate (NADPH) or an NADPH-generating reaction system thereto, and incubating the resulting mixture together with Compound (I), preferably in the presence of bovine serum albumin and a stabilizer.

As the hepatocyte microsome, a hepatocyte microsome derived from a rat, to which a drug metabolic enzyme inducer such as Phenobarbital Sodium has been administered, is preferably used. The NADPH-generating system is not specifically limited, and an example thereof is a mixed solution of 8 mM sodium β-nicotinamide adenine dinucleotide phosphate (β-NADP), 80 mM of sodium glucose-6-phosphate, 10 units of glucose 6-phosphate dehydrogenase (derived from yeast; manufactured by Oriental Yeast Co., Ltd.) and 60 mM magnesium chloride. As the stabilizer, any agent may be used so long as it can inhibit lipid peroxidation of hepatocyte microsome to stabilize the drug metabolic enzyme, and an example thereof is disodium ethylenediaminetetraacetate (EDTA). The incubation is carried out at 30 to 40° C., preferably at 37° C. and the reaction is completed in 10 minutes to 24 hours.

Conventional separation methods such as column chromatography using an ion-exchange resin, etc., high performance liquid chromatography, and crystallization can be used as the method of recovering Compound (II) from an aqueous medium or an organic solvent.
Preparation Process 2:

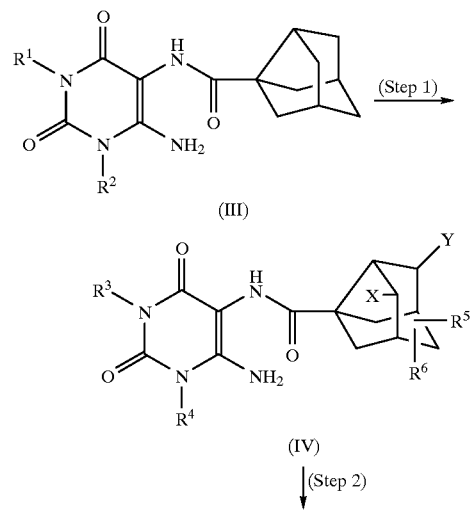

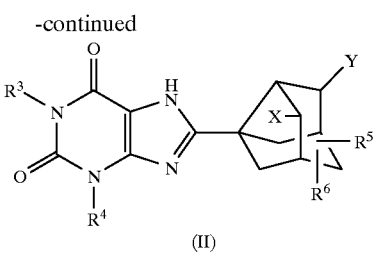

(II)

(In the formulae, $R^1$, $R^2$, $R^3$, $R^4$, $R^5$, $R^6$, X and Y have the same meanings as defined above.)

Step 1:

Compound (IV) can be obtained according to the method of Preparation Process 1 using Compound (III) obtained by a known method (Japanese Published Unexamined Patent Application No.173889/91) in place of Compound (I). In the process, a more preferable enzyme source is appropriately selected for use.

Step 2:

Compound (II) can be obtained by treating Compound (IV) in the presence of a base (method A), in the presence of a dehydrating agent (method B), or under heating (method C).

In method A, an alkali metal hydroxide such as sodium hydroxide and potassium hydroxide, or an alkaline earth metal hydroxide such as calcium hydroxide may be used as the base. As the reaction solvent, water, a lower alcohol such as methanol and ethanol, an ether such as dioxane and tetrahydrofuran, dimethylformamide, dimethyl sulfoxide, etc. may be used singly or in combination. The reaction is carried out at 0 to 180° C. and completed in 10 minutes to 6 hours.

In method B, a thionyl halide such as thionyl chloride, or phosphorus oxyhalide such as phosphorus oxychloride may be used as the dehydrating agent. The reaction is carried out in the absence of a solvent or in the presence of an inert solvent such as a halogenated hydrocarbon (e.g. methylene chloride, chloroform, or ethane dichloride), dimethylformamide, and dimethyl sulfoxide, at 0 to 180° C. and is completed in 0.5 to 12 hours.

In method C, a polar solvent such as dimethylformamide, dimethyl sulfoxide, and Dowtherm A (manufactured by Dow Chemical Co.) may be used as the reaction solvent. The reaction is carried out at 50 to 200° C. and is completed in 10 minutes to 5 hours.

The desired compounds in the present processes can be isolated and purified by purification methods conventionally used in fermentation or organic synthetic chemistry such as filtration, extraction, washing, drying, concentration, recrystallization, and various kinds of chromatography.

In the case where a salt of Compound (IIa) is desired, and it is produced in the form of the desired salt, it can be subjected to purification as such. In the case where Compound (IIa) is produced in the free state and its salt is desired, Compound (IIa) is dissolved or suspended in a suitable solvent, followed by addition of an acid or a base to form a salt.

Compound (IIa) and pharmaceutically acceptable salts thereof may also be in the form of adducts with water or various solvents, which are also within the scope of the present invention.

Compound (II) obtained as described above has adenosine $A_1$ receptor antagonizing activity, and exhibiting diuretic effect and renal-protecting effect. Therefore, Compound (II) is useful as a diuretic agent, a hypotensive agent and a therapeutic agent for edema with diuretic effect, as well as a renal-protecting agent such as a preventive and therapeutic agent for nephrotoxicity, an agent to protect renal function, a preventive and therapeutic agent for nephritis, and a preventive and therapeutic agent for nephrotic syndrome.

TABLE 1

| Compd. No. | $R^1$ | $R^2$ | Q |
|---|---|---|---|
| 1 | n-$C_3H_7$ | n-$C_3H_7$ | (adamantyl-CH(OH)H) |
| 2 | n-$C_3H_7$ | n-$C_3H_7$ | (adamantyl-CH(OH)H stereo) |

TABLE 1-continued

| Compd. No. | R¹ | R² | Q |
|---|---|---|---|
| 3 | n-C$_3$H$_7$ | n-C$_3$H$_7$ | (1-hydroxyadamantan-3-yl) |
| 4 | n-C$_3$H$_7$ | n-C$_3$H$_7$ | (adamantyl-CH(OH)-) |
| 5 | n-C$_3$H$_7$ | n-C$_3$H$_7$ | (adamantyl-CH(OH)-) |
| 6 | n-C$_3$H$_7$ | n-C$_3$H$_7$ | (dihydroxy adamantyl derivative) |
| 7 | n-C$_3$H$_7$ | CH$_3$CH(OH)CH$_2$ | (hydroxy adamantyl derivative) |
| 8 | CH$_3$CH(OH)CH$_2$ | n-C$_3$H$_7$ | (adamantyl-CH(OH)-) |
| 9 | CH$_3$CH(OH)CH$_2$ | n-C$_3$H$_7$ | (adamantyl-CH(OH)-) |

TABLE 1-continued
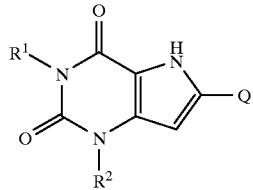
| Compd. No. | R¹ | R² | Q |
|---|---|---|---|
| 10 | CH₃CH(OH)CH₂ | n-C₃H₇ | 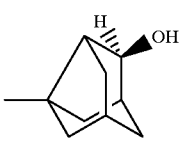 |
| 11 | CH₃COCH₂ | n-C₃H₇ | 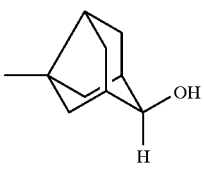 |
| 12 | CH₃COCH₂ | n-C₃H₇ | 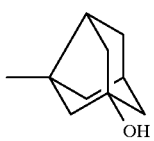 |
| 13 | CH₃COCH₂ | n-C₃H₇ | 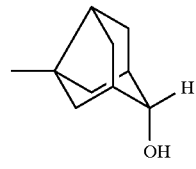 |
| 14 | CH₃COCH₂ | n-C₃H₇ | 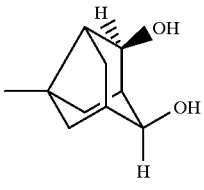 |
| 15 | CH₃COCH₂ | CH₃CH(OH)CH₂ | 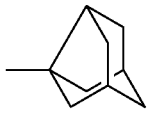 |
| 16 | CH₃COCH₂ | n-C₃H₇ | 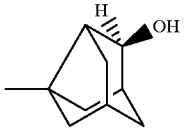 |
| 17 | H | n-C₃H₇ | 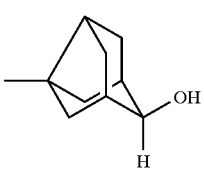 |

The pharmacological activities of Compound (II) are shown in the following test examples.

Test Example 1 Acute Toxicity Test

Test compounds were orally administered to groups of dd-strain male mice weighing 20±1 g, each group consisting of three mice. Seven days after the administration, minimum lethal dose (MLD) of each compound was determined by observing the mortality.

The MLD values of the test compounds shown in Table 1 are greater than 300 mg/kg, indicating that the toxicity of the compounds is weak. Therefore, these compounds can be safely used in a wide range of doses.

Test Example 2 Adenosine Receptor Antagonizing Activity (Adenosine $A_1$ Receptor Binding Test)

The test was conducted according to the method of Bruns et al. [Mol. Pharmacol., 29, 331 (1986)] with slight modification.

Corpus striatum of a rat was suspended in ice-cooled 50 mM Tris hydroxymethyl aminomethane hydrochloride (Tris HCl) buffer (pH 7.7) by using Polytron homogenizer (manufactured by Kinematicas Co.) The suspension was centrifuged (50,000×g, 10 minutes), and the precipitate was suspended again in the same amount of 50 mM Tris HCl buffer. The suspension was centrifuged under the same conditions, and the final precipitate was suspended once again in 50 mM Tris HCl buffer to give a tissue concentration of 100 mg (wet weight)/ml. The tissue suspension was allowed to stand at 37° C. for 30 minutes in the presence of 0.02 unit/mg tissue of adenosine deaminase (manufactured by Sigma Co.) The tissue suspension was centrifuged (50,000×g, 10 minutes) and to the obtained precipitates was added 50 mM Tris HCl buffer to give a tissue concentration of 10 mg (wet weight)/ml.

To 1 ml of the tissue suspension thus prepared were added 50 μl of cyclohexyladenosine labeled with tritium ($^3$H-CHA: 27 Ci/mmol, manufactured by New England Nuclear) (final concentration: 1.1 nM) and 50 μl of a test compound. The resulting mixture was allowed to stand at 25° C. for 90 minutes and then rapidly filtered by suction through a glass fiber filter (GF/C, manufactured by Whatman Co.) The filter was immediately washed three times with 5 ml each of ice-cooled 50 mM Tris HCl buffer, and transferred to a vial, and a scintillator (EX-H, manufactured by Wako Pure Chemical Industries, Ltd.) was added thereto. The radioactivity on the filter was determined with a liquid scintillation counter (manufactured by Packard Instrument Co.)

The inhibition rate ($K_i$ value) of the test compound against the binding of $A_1$ receptors ($^3$H-CHA binding) was calculated by the equation of Cheng-Prusoff.

$$\text{Inhibition Rate (\%)} = \left(1 - \frac{[B] - [N]}{[T] - [N]}\right) \times 100$$

[Notes]
1. "B" means the amount of radioactivity of $^3$H-CHA bound in the presence of a test compound at various concentrations.
2. "T" means the amount of radioactivity of $^3$H-CHA bound in the absence of a test compound.
3. "lN" means the amount of radioactivity of $^3$H-CHA bound in the presence of 10 μM $N^6$-(L-2-phenylisopropyl)-adenosine (Sigma Co.)

The results are shown in Table 2.

TABLE 2

| Test compound | Ki (nM) |
|---|---|
| 1 | 0.23 |
| 2 | 0.24 |
| 3 | 0.50 |
| 4 | 0.31 |
| 5 | 0.31 |

Test Example 3 Diuretic Effect

The experiment was carried out by using Wistar rats (male; 150 to 300 g). The rats were starved for 18 hours prior to the administration of a test compound (n=4 to 5). After a test compound dissolved in 0.4% methanol, 1% dimethylsulfoxde, and 0.01N sodium hydroxide/physiological saline was administered intravenously to the rat, the physiological saline (25 ml/kg) was orally administered thereto. Alternatively, a test compound dissolved in the physiological saline (25 ml/kg) was orally administered to the rats. Urine was collected from the rats during 4 hours after the oral administration, and urine volume was measured by a graduated measuring cylinder, and the electrolytes ($Na^+$ and $K^+$) in the urine were determined by flame photometer (775A, manufactured by Hitachi, Ltd.) The test results are shown in Tables 3 and 4.

TABLE 3

| Test compound | Dose (μg/kg, iv) (n = 5) | Amount of urine (ml/kg) | Amount of $Na^+$ excreted (mEq/kg) | Amount of $K^+$ excreted (mEq/kg) | $Na^+/K^+$ |
|---|---|---|---|---|---|
| Control group | — | 14.5 ± 1.8 | 2.23 ± 0.61 | 1.47 ± 0.31 | 1.52 |
| 1 | 3 | 26.4 ± 0.6* | 3.71 ± 0.12** | 1.24 ± 0.10 | 2.99 |

*p < 0.05;
**p < 0.01 (Dunnett's test)

TABLE 4

| Test compound | Dose (mg/kg, po) (n) | Increase in amount of urine Δ(%) | Increase amount of $Na^+$ excreted Δ(%) | Increase in amount of $K^+$ excreted Δ(%) | $Na^+/K^+$ |
|---|---|---|---|---|---|
| Control group | -(4–5) | 0 | 0 | 0 | 1.00 |
| 1 | 0.01(4) | 99 | 139 | 11 | 2.16 |
| 1 | 0.1(4) | 105 | 148 | −9 | 2.72 |
| 2 | 0.1(5) | 134 | 107 | 12 | 1.85 |
| 2 | 1.6(5) | 297 | 220 | 15 | 2.77 |
| 3 | 0.025(5) | 324 | 238 | 32 | 2.55 |
| 3 | 0.1(5) | 356 | 272 | 18 | 3.15 |
| 4 | 0.01(5) | 200 | 167 | 43 | 1.86 |
| 4 | 1.6(5) | 232 | 180 | 35 | 2.07 |
| 5 | 0.1(5) | 256 | 277 | 23 | 3.07 |
| 5 | 0.0025(5) | 77 | 68 | 8 | 1.56 |

As shown in Tables 3 and 4, test compounds exhibited an excellent Na-diuretic effect.

Test Example 4 Renal-Protecting Activity (Glycerol-Induced Renal Insufficiency Model)

Renal insufficiency is the condition that homeostasis of a body fluid is unable to be maintained by disorder of renal function. It is known that subcutaneous or intramuscular administration of glycerol to rats induces acute renal insufficiency characterized by renal tubular disturbance [Can. J. Physiol. Pharmacol., 65, 42 (1987)].

Male Wistar rats were fisted from both food and water for 18 hours. A test compound was intraperitoneally administered to the rats (dose; 0.1 ml/100 g). After 30 minutes, the rats were anesthetized with ether and the back skin was picked up and 0.8 ml/100 mg of 50% glycerol was subcutaneously administered. Twenty four hours after the glycerol injection, the rats were anesthetized with ether and 5 ml of blood was collected from the descending aorta. A sample of the collected blood was allowed to stand for 30 minutes or longer and then centrifuged at 3,000 rpm for 10 minutes to obtain the serum. Creatinine in the serum sample and urea nitrogen in the serum were determined with an autoanalyzer (AU510, Olympus Optical Co., Ltd.) using Olympus AU500/550 exclusive reagent "Katayama" in both of creatinine test (Jaffe' method) and urea-nitrogen test (enzyme method).

The test results were treated statistically between the control group and the test compound-administered group [significant difference test, Student's t-test (n=8 to 10)].

The test results are shown in Table 5.

TABLE 5

| Test compound | Dose (mg/kg, ip) | Amount of creatinine in serum (mg/dl) | Amount of urea-nitrogen in serum (mg/dl) |
|---|---|---|---|
| Control group | — | 4.57 ± 0.31 | 164.9 ± 10.3 |
| 2 | 1 | 1.88 ± 0.20*** | 58.0 ± 8.8*** |
| 4 | 1 | 2.00 ± 0.17*** | 76.0 ± 8.8*** |
| Control group | — | 3.57 ± 0.21 | 149.7 ± 7.0 |
| 3 | 0.03 | 1.64 ± 0.17*** | 49.0 ± 6.9*** |
| Control group | — | 4.35 ± 0.23 | 139.7 ± 10.2 |
| 1 | 0.01 | 2.00 ± 0.21**[1)] | 69.9 ± 8.4***[1)] |
| 1 | 0.1 | 2.32 ± 0.16**[1)] | 64.4 ± 4.5**[1)] |
| Control group | — | 3.90 ± 0.24 | 124.9 ± 7.5 |
| 5 | 0.01 | 2.18 ± 0.11*** | 61.3 ± 6.1*** |

***$p < 0.001$ (Student's t test);
**[1)]$p < 0.01$ (Dunnett's test)

As shown in Table 5, test compounds significantly inhibited increases in the amount of serum creatinine and that of serum urea-nitrogen by intraperitoneal administration in a dose of 1 mg/kg or less.

On the contrary, aminophylline (10 mg/kg, ip) showed only a weak inhibitory tendancy, and furosemide (10 mg/kg, ip) showed a tendancy of deterioration.

Compounds (IIa) or pharmaceutically acceptable salts thereof can be administered as they are, or in the form of various pharmaceutical compositions. The pharmaceutical compositions in accordance with the present invention can be prepared by uniformly mixing an effective amount of Compound (IIa) or a pharmaceutically acceptable salt thereof, as an active ingredient, with a pharmaceutically acceptable carrier. It is desired that such pharmaceutical compositions are prepared in a unit dose form suitable for oral administration or administration through injection.

For preparing a pharmaceutical composition for oral administration, any useful pharmaceutically acceptable carrier can be used. For example, liquid preparations for oral administration such as suspension and syrup can be prepared using water, sugars such as sucrose, sorbitol, and fructose, glycols such as polyethylene glycol and propylene glycol, oils such as sesame oil, olive oil, and soybean oil, preservatives such as p-hydroxybenzoates, flavors such as strawberry flavor and peppermint, etc. Powders, pills, capsules, and tablets can be prepared using excipients such as lactose, glucose, sucrose, and mannitol, disintegrating agents such as starch and sodium alginate, lubricants such as magnesium stearate and talc, binders such as polyvinyl alcohol, hydroxypropyl cellulose, and gelatin, surfactants such as fatty acid esters, plasticizers such as glycerin, etc. Tablets and capsules are the most useful oral unit dose forms because of the readiness of administration. For preparing tablets and capsules, solid pharmaceutical carriers are used.

Injectable preparations can be prepared using a carrier such as distilled water, a salt solution, a glucose solution or a mixture of a salt solution and a glucose solution. The preparations can be prepared in the form of solution, suspension, or dispersion according to a conventional method by using a suitable solubilizing agent or suspending agent.

Compounds (IIa) or pharmaceutically acceptable salts thereof can be administered orally in the said dosage forms or parenterally as injections. The effective dose and the administration schedule vary depending upon the mode of administration, the age, body weight, and conditions of a patient, etc. However, generally, Compound (IIa) or a pharmaceutically acceptable salt thereof is administered in a daily dose of 1 to 50 mg/kg in 3 to 4 parts.

Certain embodiments of the present invention are illustrated in the following examples and reference examples.

BEST MODE FOR CARRYING OUT THE INVENTION

EXAMPLE 1

8-(Trans-9-hydroxy-3-tricyclo[$3.3.1.0^{3,7}$]nonyl)-1,3-dipropylxanthine (Compound 1)

Each of the media (10 ml) having the following compositions was prepared, and 1,3-dipropyl-8-(3-tricyclo [$3.3.1.0^{3,7}$]nonyl)xanthine (Japanese Published Unexamined Patent Application No.173889/91) was suspended in each of the media (0.05% w/v). The media was poured into a test tube and sterilized by heating at 120° C. for 20 minutes in an autoclave.

Medium A: corn steep liquor 2%, glucose 1%, Bridge 35 (Nakarai Tesk) 0.25%, 1-adamantanamine 0.1%, pH 4.85

Medium B: corn steep liquor 4%, sucrose 1%, Bridge 35 (Nakarai Tesk) 0.25%, 1-adamantanamine 0.1%, pH 6.0

One platinum loop of each of the various types of bacteria shown in Table 6 was inoculated into the prepared medium from a slant medium, and subjected to aerobic shaking culture at 28° C. for the time shown in Table 6. Then, 2 ml of ethyl acetate was added thereto to extract the produced Compound 1 into an organic solvent layer. The obtained reaction solution was analyzed by high performance liquid chromatography (HPLC). The results obtained are shown in Table 6.

TABLE 6

| Strain | Medium | Culture time (hr.) | Yield (%) |
|---|---|---|---|
| *Beauveria bassiana* FERM BP-4607 | A | 168 | 45 |
| *Absidia ramosa* FERM BP-4605 | A | 168 | 45 |
| *Bacillus megaterium* FERM BP-4606 | B | 49 | 30 |

EXAMPLE 2

8-(Trans-9-hydroxy-3-tricyclo[$3.3.1.0^{3,7}$]nonyl)-1,3-dipropylxanthine (Compound 1), 8-(trans-6-hydroxy-3- tricylco[3.3.1.0$^{3,7}$]nonyl)-1,3-dipropylxanthine (Compound 2), and 8-(1-hydroxy-3-tricyclo[3.3.1.0$^{3,7}$]nonyl)-1,3-dipropylxanthine (Compound 3)

6-Amino-5-(noradamantan-3-ylcarbonylamino)-1,3-dipropyluracil (6-amino-1,3-dipropyl-5-(3-tricyclo[3.3.1.0$^{3,7}$]nonylcarbonylamino)uracil (Japanese Published Unexamined Patent Application No.173889/91) (3.00 g, 8.02 mmol) was added to 3 L of the medium at pH 4.85 containing 2% of corn steep liquor, 1% of glucose, and 0.1% of 1-adamantanamine in a 5 L jar. The medium was sterilized by heating and then cooled, and *Beauveria bassiana* FERM BP-4607 (deposited Mar. 16, 1994 in the National Institute of Bioscience and Human-Technology, Agency of Industrial Science and Technology, 1–3, Higashi 1-chome, Tsukuba-shi, Ibaraki-ken, 305 Japan), which was a kind of mold, was inoculated into the medium. After culture was carried out at 28° C., 150 rpm for 8 days (during this time, sterilized air was passed at a rate of 3 L/min), 1 L of ethyl acetate was added to the medium to extract the reaction product into an organic solvent layer. The extract was concentrated under reduced pressure, and the residue was purified by silica gel column chromatography (eluent: hexane/ethyl acetate=1/1 V/V) to give 2.3 g of a white powder. The powder was suspended in 100 ml of water, and 3.0 g of calcium hydroxide was added thereto, followed by heating under reflux for 3.5 hours. After cooling to 0° C., the reaction solution was made acidic by addition of concentrated hydrochloric acid, followed by extraction with chloroform. The extract was concentrated under reduced pressure, and the residue was purified by silica gel column chromatography (eluent: hexane/ethyl acetate=2/1 V/V) to give 340 mg of a mixture of Compound 1 and Compound 3, and 610 mg (yield 20%) of Compound 2 as white powders, respectively.

Then, the mixture of Compound 1 and Compound 3 was purified by HPLC [column: YMC-Pack, SH-365-10, S-10 (manufactured by YMC Co., Ltd.) 30 mm i.d.×500 mm; eluent: 50% acetonitrile/water; flow rate: 80 ml/min] to give 280 mg (yield 9.4%) of Compound 1 and 40 mg (yield 1.3%) of Compound 3 as white powders, respectively.

Compound 1:

Melting point: 224.9–225.3° C. Elemental analysis: $C_{20}H_{28}N_4O_3$ Calcd.(%): C 64.49, H 7.58, N 15.04 Found (%): C 64.74, H 7.37, N 15.15 IR (KBr) $v_{max}$ (cm$^{-1}$): 1696, 1653, 1555, 1508, 1495 $^1$H-NMR (270 MHz; CD$_3$OD) δ(ppm): 4.07(2H, m), 3.95(2H, m), 3.89(1H, br.t, J=3.0 Hz), 2.62(1H, tt, J=6.7, 1.4 Hz), 2.34(2H, br.s), 2.17(2H, m), 2.10(2H, dd, J=11.3, 2.8 Hz), 1.98(2H, dd, J=10.9, 2.7 Hz), about 1.81(2H, m), 1.77(2H, m), 1.66(2H, m), 0.95(3H, t, J=7.4 Hz), 0.94(3H, t, J=7.5 Hz) $^{13}$C-NMR (270 MHz; CD$_3$OD) δ(ppm): 161.8, 156.1, 153.0, 149.8, 108.4, 73.2, 49.5, 46.6, 46.3, 46.1, 44.9, 43.9, 39.7, 22.41, 22.36, 11.5, 11.4 MS (EI) m/e (relative intensity): 372(100, M$^+$), 330 (59), 302(27), 288(63), 258(17)

Compound 2:

Melting point: 192.8–193.5° C. Elemental analysis: $C_{20}H_{28}N_4O_3$ Calcd.(%): C 64.49, H 7.58, N 15.04 Found (%): C 64.78, H 7.81, N 15.20 IR (KBr) $v_{max}$ (cm$^{-1}$): 1703, 1654, 1553, 1500 $^1$H-NMR (270 MHz; CD$_3$OD) δ(ppm): 4.22(1H, dd, J=6.9, 3.3 Hz), 4.07(2H, m), 3.95(2H, m), 2.59(1H, tt, J=6.9, 1.3 Hz), 2.51(1H, dd, J=11.4, 2.1 Hz), 2.30 (1H, m), about 2.18(2H, m), 2.10(1H, m), about 2.02 (1H, m), about 1.97(1H, m), 1.91(1H, d, J=11.5 Hz), 1.78 (2H, m), 1.66(2H, m), about 1.55 (1H, m), about 1.48(1H, m), 0.95(3H, t, J=7.4 Hz), 0.94(3H, t, J=7.4 Hz) $^{13}$C-NMR (270 MHz; CD$_3$OD) δ(ppm): 161.9, 156.1, 153.0, 149.8, 108.4, 76.5, 49.4, 49.3, 46.1, 43.9, 43.7, 41.9, 38.2, 34.1, 30.4, 22.4, 22.3, 11.5, 11.3 MS (EI) m/e (relative intensity): 372(100, M$^+$), 370(81), 354(44), 330(50), 328(54), 288(81), 286(64)

Compound 3:

Melting point: 174.8–177.2° C. IR (KBr) $v_{max}$ (cm$^{-1}$): 1694, 1648, 1550, 1498 $^1$H-NMR (270 MHz; CD$_3$OD) δ(ppm): 4.07(2H, m), 3.95(2H, m), 2.71(1H, dt, J=6.8, 1.5 Hz), 2.52(1H, m), 2.34(1H, m), 2.13(1H, m), 2.08(1H, m), 1.94–1.84(5H, m), 1.78(2H, m), 1.66(2H, m), 1.64–1.58(1H, m), 1.58 (1H, dd, J=10.6, 3.0 Hz), 0.95(3H, t, J=7.4 Hz), 0.94(3H, t, J=7.4 Hz) $^{13}$C-NMR (270 MHz; CD$_3$OD) δ(ppm): 161.4, 156.1, 153.0, 149.8, 108.5, 77.3, 54.4, 49.7, 48.7, 46.1, 45.5, 43.9, 43.3, 43.1, 38.5, 22.41, 22.35, 11.5, 11.4 MS (EI) m/e (relative intensity): 372(100, M$^+$), 355 (21), 330(73), 302(23), 288(65) HR-MS m/e: Calcd. ($C_{20}H_{28}N_4O_3$) 372.2161; Found 372.2151

EXAMPLE 3

8-(Trans-9-hydroxy-3-tricyclo[3.3.1.0$^{3,7}$] nonyl)-1,3-dipropylxanthine (Compound 1), 8-(cis-9-hydroxy-3-tricyclo[3.3.1.0$^{3,7}$]nonyl)-1,3-dipropylxanthine (Compound 4), and 8-(trans-6-hydroxy-3-tricyclo[3.3.1.0$^{3,7}$]nonyl)-1,3-dipropylxanthine (Compound 2)

1,3-Dipropyl-8-(3-tricyclo[3.3.1.0$^{3,7}$]nonyl)-xanthine (50 mg, 0.14 mmol) was added to 100 ml of the medium at pH 6 containing 4% of corn steep liquor, 3% of sucrose, 0.25% of Bridge 35 (Nakarai Tesk), and 0.075% of 1-adamantanamine. The medium was sterilized by heating and then cooled, and *Bacillus megaterium* FERM BP-4606 (deposited Mar. 16, 1994 in the National Institute of Bioscience and Human-Technology, Agency of Industrial Science and Technology, 1–3, Higashi 1-chome, Tsukuba-shi, Ibaraki-ken, 305 Japan), which was a kind of bacteria, was inoculated into the medium. After shaking culture was carried out at 28° C. for 3 days, 5 ml of ethyl acetate was added to the medium to extract the reaction product into an organic solvent layer.

The extract was purified by silica gel column chromatography (eluent: hexane/acetic acid=2/1 V/V) to give 14.7 mg (yield 29%) of Compound 1, 4.5 mg (yield 8.9%) of Compound 4, and 0.35 mg (yield 0.68%) of Compound 2 as white powders, respectively.

Compound 4:

Melting point: 224.8–225.1° C. Elemental analysis: $C_{20}H_{28}N_4O_3$ Calcd.(%): C 64.49, H 7.58, N 15.04 Found (%): C 64.58, H 8.01, N 14.94 IR (KBr) $v_{max}$ (cm$^{-1}$): 1694, 1650, 1499 $^1$H-NMR (270 MHz; CD$_3$OD) δ(ppm): 4.08(2H, m), 3.95(2H, m), 3.86(1H, m), 2.68(1H, bt, J=6.6 Hz), 2.36(2H, m), about 2.35(2H, m), 2.01–1.90(4H, m), 1.78 (2H, m), 1.66(2H, m), about 1.65(2H, m), 0.96(3H, t, J=7.4 Hz), 0.94(3H, t, J=7.4 Hz) $^{13}$C-NMR (270 MHz; CD$_3$OD) δ(ppm): 161.9, 156.1, 153.0, 149.8, 108.4, 72.7, 49.8, 46.1, 45.2, 45.1, 44.8, 43.9, 41.3, 22.41, 22.35, 11.5, 11.3 MS (EI) m/e (relative intensity): 372(100, M$^+$), 330(26), 302(10), 288(44), 258(18)

EXAMPLE 4

8-(Trans-9-hydroxy-3-tricyclo[3.3.1.0$^{3,7}$]nonyl)-1,3-dipropylxanthine (Compound 1)

1,3-Dipropyl-8-(3-tricyclo[3.3.1.0$^{3,7}$]nonyl)-xanthine (50 mg, 0.14 mmol) was added to 100 ml of the medium at pH 4.85 containing 2% of corn steep liquor, 3% of glucose, 0.25% of Bridge 35 (Nakarai Tesk), and 0.01% of 1-adamantanamine. The medium was sterilized by heating and then cooled, and *Absidia ramosa* FERM BP-4605 (deposited Mar. 16, 1994 in the National Institute of Bioscience and Human-Technology, Agency of Industrial Science and Technology, 1–3, Higashi 1-chome, Tsukuba-shi, Ibaraki-ken, 305 Japan), which was a kind of bacteria, was inoculated into the medium. After shaking culture was carried out at 28° C. for 5 days, 50 ml of ethyl acetate was added to the medium to extract the reaction product into an organic solvent layer. The extract was treated by the same method as that employed in Example 3 to give 39 mg (yield 75%) of Compound 1 as a white powder.

EXAMPLE 5

8-(Trans-9-hydroxy-3-tricyclo[3.3.1.0$^{3,7}$]nonyl)-1,3-dipropylxanthine (Compound 1)

1,3-Dipropyl-8-(3-tricyclo[3.3.1.0$^{3,7}$]nonyl)-xanthine (30 mg, 0.084 mmol) was added to 30 ml of the medium at pH 4.85 containing 2% of corn steep liquor, 1% of glucose, 0.25% of Bridge 35 (Nakarai Tesk), and 0.1% of 1-adamantanamine. The medium was sterilized by heating and then cooled, and *Beauveria bassiana* IFO-4848, which was a kind of mold, was inoculated into the medium. After shaking culture was carried out at 28° C. for 9 days, 15 ml of ethyl acetate was added to the medium to extract the reaction product into an organic solvent layer. The extract was treated by the same method as that employed in Example 3 to give 10 mg (yield 32%) of Compound 1 as a white powder.

EXAMPLE 6

8-(Trans-9-hydroxy-3-tetracyclo[3.3.1.0$^{3,7}$.0$^{6,8}$]-nonyl)-1,3-dipropylxanthine (Compound 5), 8-(trans-6, trans-9-dihydroxy-r-3-tricylco[3.3.1.0$^{3,7}$]nonyl)-1,3-dipropylxanthine (Compound 6), and 3-(2-hydroxypropyl)-8-(trans-6-hydorxy-3-tricyclo[3.3.1.0$^{3,7}$]nonyl)-1-propylxanthine (Compound 7)

6-Amino-1,3-dipropyl-5-(3-tricyclo[3.3.1.0$^{3,7}$]-nonylcarbonylamino) uracil [6-amino-5-(noradamantan-3-ylcarbonylamino)-1,3-dipropyluracil; Compound A] (Japanese Published Unexamined Patent Application No.173889/91) (3.00 g, 8.02 mmol) was added to 3 L of the medium at pH 4.85 containing 2% of corn steep liquor, 1% of glucose, and 0.1% of 1-adamantanamine in a 5 L jar. The medium was sterilized by heating and then cooled, and *Beauveria bassiana* FERM BP-4607, which was a kind of mold, was inoculated into the medium. After culture was carried out at 28° C., 150 rpm for 8 days (during this time, sterilized air was passed at a rate of 3 L/min), 1 L of ethyl acetate was added to the medium to extract the reaction product into an organic solvent layer. The extract was concentrated under reduced pressure, and the residue was purified by silica gel column chromatography (eluent: hexane/ethyl acetate=1/1 V/V) to give 2.3 g of a white power. The powder was suspended in 100 ml of water, and 3.0 g of calcium hydroxide was added thereto, followed by heating under reflux for 3.5 hours. After cooling to 0° C., the reaction solution was made acidic by addition of concentrated hydrochloric acid, followed by extraction with chloroform. The same procedure as described above was further repeated four times by using 3.00 g (8.02 mmol) of Compound A. All extracts (5 times of procedures) were combined and concentrated under reduced pressure, and the residue was purified by silica gel column chromatography (eluent: hexane/ethyl acetate=2/1 V/V) to give about 150 mg of a crude product of Compound 5 as an oily substance.

Then, the crude product was purified by HPLC [column: YMC-Pack, SH-365-10, S-10 (manufactured by YMC Co., Ltd.) 30 mm i.d.×500 mm; eluent: 30% acetonitrile/water; flow rate: 40 ml/min] to give 41.3 mg of Compound 5, 4.6 mg of Compound 6, and 4.9 mg of Compound 7 as white powders, respectively.

Compound 5:
Melting point: 218.7–219.8° C. IR (KBr) $v_{max}$ (cm$^{-1}$): 1699, 1653, 1554, 1499 $^1$H-NMR (270 MHz; CD$_3$OD) δ(ppm): 4.06(2H, m), 3.94(2H, m), 3.75(1H, brs), 2.62(2H, m), 2.51(1H, t, J=6.8 Hz), about 2.34(2H, dd, J=6.8, 3.5 Hz), about 2.30(2H, m), 1.78(2H, m), 1.77(2H, d, J=11.2 Hz), 1.66(2H, m), 0.96(3H, t, J=7.4 Hz), 0.94(3H, t, J=7.4 Hz) $^{13}$C-NMR (270 MHz; CD$_3$OD) δ(ppm): 159.1, 156.1, 152.9, 149.6, 108.5, 86.5, 51.4, 50.1(×2), 49.2(×2), 46.1, 43.9, 43.8, 37.2(×2), 22.4, 22.3, 11.5, 11.3 HR-MS m/e: Calcd. (C$_{20}$H$_{26}$N$_4$O$_3$) 370.2005; Found 370.1997

Compound 6:
Melting point: 197.7–198.9° C. IR (KBr) $v_{max}$ (cm$^{-1}$): 1696, 1654, 1554, 1499 $^1$H-NMR (270 MHz; CD$_3$OD) δ(ppm): 4.30(1H, m), 4.07(2H, m), 3.95(2H, m), 3.90(1H, m), 2.76(1H, dd, J=12.2, 2.8 Hz), 2.61(1H, t, J=6.8 Hz), 2.41(1H, m), 2.35 (1H, m), 2.27(1H, dt, J=11.5, 3.6 Hz), 2.12(1H, dt, J=11.8, 3.6 Hz), 1.96(1H, dd, J=11.5, 2.8 Hz), 1.79 (1H, m), 1.78(2H, m), 1.66(2H, m), 0.95(3H, t, J=7.4 Hz), 0.94(3H, t, J=7.4 Hz) $^{13}$C-NMR (270 MHz; CD$_3$OD) δ(ppm): 160.8, 156.1, 153.0, 149.7, 108.5, 78.7, 75.5, 49.3, 48.7, 47.1, 46.1, 45.5, 45.0, 43.9, 40.1, 30.2, 22.4, 22.3, 11.5, 11.3 HR-MS m/e: Calcd. (C$_{20}$H$_{28}$N$_4$O$_4$) 388.2111; Found 388.2132

Compound 7:
Melting point: 188.1–191.2° C. IR (KBr) $v_{max}$ (cm$^{-1}$): 1702, 1649, 1544, 1501 $^1$H-NMR (270 MHz; CD$_3$OD) δ(ppm): 4.24(1H, m), 4.21(1H, m), 4.18(1H, m), 4.04(1H, m), 3.95(2H, m), 2.58(1H, t, J=6.8 Hz), 2.51(1H, dd, J=11.2, 2.3 Hz), 2.30(1H, m), about 2.18(2H, m), 2.09(1H, m), 2.02(1H, m), 1.97(1H, m), 1.90(1H, d, J=11.5 Hz), 1.66(2H, m), 1.48(2H, m), 1.21(3H, d, J=6.3 Hz), 0.94(3H, t, J=7.4 Hz) $^{13}$C-NMR (270 MHz; CD$_3$OD) δ(ppm): 161.6, 156.1, 153.4, 150.0, 108.4, 78.8, 66.5, 51.3, 49.4, 49.3, 44.0, 43.6, 41.9, 34.1, 38.2, 30.8, 22.3, 20.9, 11.5 HR-MS m/e: Calcd. (C$_{20}$H$_{28}$N$_4$O$_4$) 388.2111; Found 388.2118

EXAMPLE 7

8-(Trans-9-hydroxy-3-tricyclo[3.3.1.0$^{3,7}$]nonyl)-1,3-dipropylxanthine (Compound 1)

1) Preparation of rat liver microsome

Phenobarbital Sodium (manufactured by Wako Pure Chemical Industries, Ltd.) was intraperitoneally administered to male rats (SD strain, SLC, 200–220 g) at a dose of 80 mg/kg once a day for 3 days. The liver was taken out of the rat on the fourth day, and suspended in ice-cooled 1.15% potassium chloride—0.01M phosphate buffer (pH 7.4), having the 3-fold volume of the weight of the liver, with Teflon homogenizer. The suspension was centrifuged (10,000×g, 10 min, 4° C.), and the supernatant was further centrifuged (105,000×g, 60 min, 4° C.). The precipitate was suspended again in the same amount of 1.15% potassium chloride—0.01M phosphate buffer (pH 7.4), and centrifuged (40,000× g, 30 min, 4° C.). The obtained precipitate was suspended again in 20% glycerol and 0.1 mM disodium ethylenediaminetetraacetate (EDTA)—0.01M phosphate buffer (pH 7.4) to a final concentration of 10 mg (wet weight)/ml to give rat liver microsome.

2) Synthesis of Compound 1 by using rat liver microsome
1,3-Dipropyl-8-(3-tricyclo[3.3.1.0$^{3,7}$]nonyl)-xanthine (3.6 mg, 0.01 mmol) was dissolved in 1 ml of methanol, and 10 ml of the obtained rat liver microsome, 5 ml of 4% bovine serum albumin (BSA)/0.2M phosphate buffer (pH 7.4), 2 ml of NADPH-generating system mixture [8 mM sodium β-nicotinamide adenine dinucleotide phosphate (β-NADP), 80 mM sodium glucose-6-phosphate, 10 units of glucose-6-phosphate dehydrogenase (derived from yeast; manufactured by Oriental Yeast Co., Ltd.), and 60 mM magnesium chloride], and 2 ml of 1 mM EDTA were added thereto, followed by incubation at 37° C. for one hour. After centrifugation (40,000×g, 30 min, 4° C.), the supernatant was collected, and the obtained precipitate was suspended again in a 0.2M phosphate buffer. To the suspension, 5 ml of 4% bovine serum albumin (BSA)/0.2M phosphate buffer (pH 7.4), 2 ml of NADPH-generating system mixture [8 mM β-NADP, 80 mM sodium glucose-6-phosphate, 10 units of glucose-6-phosphate dehydrogenase (derived from yeast; manufactured by Oriental Yeast Co., Ltd.), and 60 mM magnesium chloride], and 2 ml of 1 mM EDTA were added again and centrifuged (40,000×g, 30 min, 4° C.) again, and the supernatant was collected. This procedure was further repeated four times, and all the supernatants were combined. Then, 600 μl of 2N aqueous solution of sodium hydroxide and 20 ml of ethyl acetate were added thereto and the mixture was shaken and stirred. The organic layer was separated by centrifugation (2500 rpm×5 min) and concentrated. The residue was purified by HPLC [column: YMC AM-312 (ODS) 5 μm (manufactured by YMC Co., Ltd.) 6 mm i.d.×150 mm; eluent: 40% acetonitrile/50 mM aqueous solution of ammonium acetate; flow rate: 1 ml/min] to give about 400 μg (yield about 10%) of Compound 1 as a white powder.

EXAMPLE 8

8-(Trans-9-hydroxy-3-tricyclo[3.3.1.0$^{3,7}$]nonyl)-1,3-dipropylxanthine (Compound 1) and 8-(trans-6, trans-9-dihydroxy-r-3-tricyclo[3.3.1.0$^{3,7}$]nonyl)-1,3-dipropylxanthine (Compound 6)

1,3-Dipropyl-8-(3-tricyclo[3.3.1.0$^{3,7}$]nonyl)-xanthine (1.50 g, 4.01 mmol) was added to 3 L of the medium at pH 4.85 containing 2% of corn steep liquor, 2% of soybean meal, 1% of glucose, and 0.0025% of copper sulfate heptahydrate. The medium was sterilized by heating and then cooled, and *Absidia ramosa* FERM BP-4605, which was a kind of mold, was inoculated into the medium. After culture was carried out at 28° C., 300 rpm for 5 days (during this time, sterilized air was passed at a rate of 3 L/min), 1 L of ethyl acetate was added to the medium to extract the reaction product into an organic solvent layer. The extract was concentrated under reduced pressure, and the residue was purified by silica gel column chromatography (eluent; chloroform/methanol=96/4 V/V) to give 410 mg of a mixture of Compound 1 and Compound 6 as a white powder. Then, the mixture was purified by silica gel column chromatography (eluent: hexane/ethyl acetate=1/3 V/V) to give 230 mg (yield 15%) of Compound 1 and 5.5 mg (yield 0.4%) of Compound 6 as white powders, respectively.

EXAMPLE 9

1-(2-Hydroxypropyl)-8-(trans-9-hydroxy-3-tricyclo [3.3.1.0$^{3,7}$]nonyl)-3-propylxanthine (Compound 8), 1-(2-hydroxypropyl)-8-(cis-9-hydroxy-3-tricyclo[3.3.1.0$^{3,7}$]nonyl)-3-propylxanthine (Compound 9), 1-(2-hydroxypropyl)-8-(trans-6-hydroxy-3-tricyclo[3.3.1.0$^{3,7}$]nonyl)-3-propylxanthine (Compound 10), and 8-(trans-9-hydroxy-3-tricyclo[3.3.1.0$^{3,7}$]nonyl)-1-(2-oxopropyl)-3-propylxanthine (Compound 11)

Compound D (3.00 g, 8.06 mmol) obtained in Reference Example 2 was added to 3 L of the medium at pH 4.85 containing 2% of corn steep liquor, 2% of soybean meal, 1% of glucose, and 0.05% of Bridge 35 (Nakarai Tesk). The medium was sterilized by heating and then cooled, and *Absidia ramosa* FERM BP-4605, which was a kind of mold, was inoculated into the medium. After culture was carried out at 28° C. for 7 days, 1 L of ethyl acetate was added to the medium to extract the reaction product into an organic solvent layer. The extract was concentrated under reduced pressure, and the residue was purified by silica gel column chromatography (eluent; chloroform/methanol=92/8 V/V) and then HPLC [column: YMC-Pack, SH-365-10, S-10 (manufactured by YMC Co., Ltd.) 30 mm i.d.×500 mm; eluent: 20% acetonitrile/water; flow rate: 40 ml/min] to give 900 mg (yield 28.8%) of Compound 8, 5.0 mg (yield 0.16%) of Compound 9, 2.0 mg (yield 0.06%) of Compound 10, and 165 mg (yield 5.3%) of Compound 11 as white powders, respectively.

Compound 8:

Melting point: 210.2–214.8° C. IR (KBr) $v_{max}$ (cm$^{-1}$): 1701, 1642, 1495 $^1$H-NMR (270 MHz; CD$_3$OD) δ(ppm): 4.15–4.05(2H, m), 4.07 (2H, t, J=7.4 Hz), 3.95–3.86(1H, m), 3.88(1H, m), 2.61(1H, t, J=6.5 Hz), 2.33(2H, m), 2.17(2H, m), 2.10(2H, m), 1.97(2H, dd, J=10.4, 2.6 Hz), 1.85–1.70 (4H, m), 1.18(3H, d, J=7.0 Hz), 0.95(3H, t, J=7.4 Hz) MS (EI) m/e: 388(M$^+$) HR-MS m/e: Calcd. (C$_{20}$H$_{28}$N$_4$O$_4$) 388.2111; Found 388.2102

Compound 9:

Melting point: 221.8–222.6° C. IR (KBr) $v_{max}$ (cm$^{-1}$): 1706, 1645, 1500 $^1$H-NMR (270 MHz; CD$_3$OD) δ(ppm): 4.15–4.05(2H, m), 4.07 (2H, t, J=7.4 Hz), 3.94–3.85(1H, m), 3.86(1H, m), 2.67(1H, t, J=6.4 Hz), 2.35(2H, m), 2.34(2H, m), 2.01–1.90(4H, m), 1.77(2H, m), 1.65(2H, dd, J=11.4, 3.0 Hz), 1.18(3H, d, J=6.9 Hz), 0.96(3H, t, J=7.4 Hz) MS (EI) m/e: 388(M$^+$)

Compound 10:

Melting point: 200.1–201.0° C. IR (KBr) $v_{max}$ (cm$^{-1}$): 1699, 1647, 1498 $^1$H-NMR (270 MHz; CD$_3$OD) δ(ppm): 4.22(1H, dd, J=6.9, 3.3 Hz), 4.15–4.05(2H, m), 4.07(2H, t, J=7.4 Hz), 3.89(1H, m), 2.58(1H, t, J=6.9 Hz), 2.51(1H, dd, J=11.3, 2.0 Hz), 2.30(1H, m), 2.20(2H, m), 2.10(1H, m), 2.05–1.95(2H, m), 1.91(1H, d, J=11.4 Hz), 1.77 (2H, m), 1.60–1.52(1H, m), 1.48(1H, m), 1.18(3H, d, J=7.0 Hz), 0.95(3H, t, J=7.4 Hz) MS (EI) m/e: 388(M$^+$)

Compound 11:

Melting point: 254.8–256.8° C. IR (KBr) $v_{max}$ (cm$^{-1}$): 1720, 1703, 1655, 1499 $^1$H-NMR (270 MHz; CD$_3$OD) δ(ppm): 4.84(2H, s), 4.07(2 H, t, J=7.4 Hz), 3.89(1H, m), 2.63(1H, t, J=7.0 Hz), 2.33 (2H, m), 2.24(3H, s), 2.17(2H, m), 2.10(2H, m), 1.99(2H, dd, J=10.9, 2.8 Hz), 1.85–1.70 (4H, m), 0.95(3H, t, J=7.4 Hz) MS (EI) m/e: 386(M$^+$) HR-MS m/e: Calcd. (C$_{20}$H$_{26}$N$_4$O$_4$) 386.1952; Found 386.1946

EXAMPLE 10

8-(Trans-9-hydroxy-3-tricyclo[3.3.1.0$^{3,7}$]nonyl)-1-(2-oxopropyl)-3-propylxanthine (Compound 11), 8-(1-hydroxy-3-tricyclo[3.3.1.0$^{3,7}$]nonyl)-1-(2-oxopropyl)-3-propylxanthine (Compound 12), 8-(cis-9-hydroxy-3-tricyclo[3.3.1.0$^{3,7}$]nonyl)-1-(2-oxopropyl)-3-propylxanthine (Compound 13), 8-(trans-6, trans-9-dihydroxy-r-3-tricyclo[3.3.1.0$^{3,7}$]nonyl)-1-(2-oxopropyl)-3-propylxanthine (Compound 14), and 3-(2-hydroxypropyl-1-(2-oxopropyl)-8-(3-tricyclo[3.3.1.0$^{3,7}$]nonyl)-xanthine (Compound 15)

Compound C (3.00 g, 8.11 mmol) obtained in Reference Example 1 was added to 3 L of the medium at pH 4.85 containing 2% of corn steep liquor, 2% of soybean meal, 1% of glucose, and 0.05% of Bridge 35 (Nakarai Tesk). The medium was sterilized by heating and then cooled, and *Absidia ramosa* FERM BP-4605, which was a kind of mold, was inoculated into the medium. After culture was carried out at 28° C. for 8 days, 1 L of ethyl acetate was added to the medium to extract the reaction product into an organic solvent layer. The extract was concentrated under reduced pressure, and the residue was purified by silica gel column chromatography (eluent; chloroform/methanol=94/6 V/V) and then HPLC [column: YMC-Pack, SH-365-10, S-10 (manufactured by YMC Co., Ltd.) 30 mm i.d.×500 mm; eluent: 20% acetonitrile/water; flow rate: 40 ml/min] to give 1.17 g (yield 37.4%; a white powder) of Compound 11, 10.1 mg (yield 0.32%; a white powder) of Compound 12, 7.3 mg (yield 0.23%, a white powder) of Compound 13, 6.6 mg (yield 0.20%; oily) of Compound 14, and 2.2 mg (yield 0.07%; oily) of Compound 15.

Compound 12:

Melting point: 224.1–226.9° C. IR (KBr) $v_{max}$ (cm$^{-1}$): 1720, 1703, 1652, 1502 $^1$H-NMR (270 MHz; CD$_3$OD) δ(ppm): 4.83(2H, s), 4.07(2H, t), 2.72(1H, t, J=6.0 Hz), 2.52(1H, m), 2.34(1H, m), 2.24(3H, s), 2.13(1H, m), 2.08 (1H, m), 1.95–1.82 (5H, m), 1.78(2H, m), 1.64–1.56(1H, m), 1.58(1H, dd, J=10.3, 3.0 Hz), 0.95(3H, t, J=7.4 Hz) HR-MS m/e: Calcd. (C$_{20}$H$_{26}$N$_4$O$_4$) 386.1952; Found 386.1968

Compound 13:

Melting point: 238.1–241.8° C. IR (KBr) $v_{max}$ (cm$^{-1}$): 1718, 1705, 1650, 1494 $^1$H-NMR (270 MHz; CD$_3$OD) δ(ppm): 4.83(2H, s), 4.07(2H, t, J=7.4 Hz), 3.86(1H, m), 2.68(1H, t, J=6.4 Hz), 2.36 (2H, m), 2.35(2H, m), 2.23(3H, s), 2.01–1.90(4H, m), 1.77(2H, m), 1.65(2H, dd, J=11.3, 2.9 Hz), 0.95 (3H, t, J=7.4 Hz) MS (EI) m/e: 386(M$^+$) HR-MS m/e: Calcd. (C$_{20}$H$_{26}$N$_4$O$_4$) 386.1952; Found 386.1948

Compound 14:

$^1$H-NMR (270 MHz; CD$_3$OD) δ(ppm): 4.83(2H s), 4.30 (1H, m), 4.08(2H, m), 3.89(1H, m), 2.76(1H, brdd, J=12.2, 2.8 Hz), 2.61(1H, t, J=6.8 Hz), 2.41(1H, m), 2.35 (1H, m), 2.27(1H, dt, J=11.5, 3.6 Hz), 2.23(3H, s), 2.12(1H, dt, J=11.8, 3.6 Hz), 1.96(1H, dd, J=11.5, 2.8 Hz), 1.79(1H, m), 1.78(2H, m), 1.63(1H, m), 0.95(3H, t, J=7.4 Hz) FABHR-MS m/e: Calcd. (C$_{20}$H$_{27}$N$_4$O$_5$) 403.1981; Found 403.1985

Compound 15:

$^1$H-NMR (270 MHz; CD$_3$OD) δ(ppm): 4.83(2H, s), 4.24 (1H, m), 4.18(1H, m), 4.04(1H, m), 2.83(1H, t, J=6.0 Hz), 2.40(2H, m), 2.24(3H, s), 2.20(2H, m), 2.03(2H, dd, J=10.7, 2.6 Hz), 1.98(2H, m), 1.80–1.70(4H, m), 1.20(3H, d, J=6.4 Hz) HR-MS m/e: Calcd. (C$_{20}$H$_{26}$N$_4$O$_4$) 386.1952; Found 386.1949

EXAMPLE 11

8-(Trans-9-hydroxy-3-tricyclo[3.3.1.0$^{3,7}$]nonyl)-1,3-dipropylxanthine (Compound 1)

1,3-Dipropyl-8-(3-tricyclo[3.3.1.0$^{3,7}$] nonyl)-xanthine (9.0 g, 25 mmol) was added to 18 L of the medium at pH 4.85 containing 2% of corn steep liquor, 3% of glucose, 0.25% of Bridge 35 (Nakarai Tesk), and 0.01% of 1-adamantanamine in a 30 L jar. The medium was sterilized by heating and then cooled, and *Absidia ramosa* FERM BP-4605, which was a kind of mold, was inoculated into the medium. After culture was carried out at 28° C., 300 rpm for 5 days (during this time, sterilized air was passed at a rate of 12 L/min), 1-propanol was added to the medium to extract the reaction product. The extract was adsorbed on synthetic adsorbent Diaion HP-20 (manufactured by Mitsubishi Kasei Industry Co., Ltd.), and an active fraction was eluted with methanol. The eluted fractions were concentrated and the obtained crude crystals were recrystallized from acetone to give 2.5 g (HPLC purity: 90%; yield 27%) of Compound 1 as a white powder.

EXAMPLE 12

1-(2-Hydroxypropyl)-8-(trans-9-hydroxy-3-tricyclo [3.3.1.0$^{3,7}$]nonyl)-3-propylxanthine (Compound 8), 8-(trans-9-hydroxy-3-tricyclo[3.3.1.0$^{3,7}$]nonyl)-1-(2-oxopropyl)-3-propylxanthine (Compound 11), 8-(1-hydroxy-3-tricyclo[3.3.1.0$^{3,7}$]nonyl)-1-(2-oxopropyl)-3-propylxanthine (Compound 12), 8-(cis-9-hydroxy-3-tricyclo[3.3.1.0$^{3,7}$]nonyl)-1-(2-oxopropyl)-3-propylxanthine (Compound 13), 8-(trans-6-hydroxy-3-tricyclo[3.3.1.0$^{3,7}$]nonyl)-1-(2-oxopropyl)-3-propylxanthine (Compound 16), and 8-(trans-9-hydroxy-3-tricyclo[3.3.1.0$^{3,7}$]nonyl)-3-propylxanthine (Compound 17)

Compound C (3.00 g, 8.11 mmol) obtained in Reference Example 1 was added to 3 L of the medium at pH 4.85 containing 2% of corn steep liquor, 2% of soybean meal, 1% of glucose, and 0.05% of Bridge 35 (Nakarai Tesk). The medium was sterilized by heating and then cooled, and *Absidia ramosa* FERM BP-4605, which was a kind of mold, was inoculated into the medium. After culture was carried out at 28° C. for 8 days, 1 L of ethyl acetate was added to the medium to extract the reaction product into an organic solvent layer. The extract was concentrated under reduced pressure and the residue was purified by HPLC [column: YMC-Pack, SH-365-10, S-10 (manufactured by YMC Co., Ltd.) 30 mm i.d.×500 mm; eluent: 20–30% acetonitrile/water (gradation over 45 min); flow rate: 40 ml/min] to give 42 mg (yield 1.34%; a white powder) of Compound 8, 1.92 g (yield 61.4%; a white powder) of Compound 11, 23 mg (yield 0.73%; a white powder) of Compound 12, 47 mg (yield 1.50%, a white powder) of Compound 13, 26 mg (yield 0.83%; a white powder) of Compound 16, and 47 mg (yield 1.76%; a pale brown powder) of Compound 17.

Compound 16:

Melting point: 214.6–215.7° C. IR (KBr) $v_{max}$ (cm$^{-1}$): 1720, 1703, 1650, 1498 $^1$-NMR (400 MHz; CD$_3$OD) δ(ppm): 4.84(2H, s), 4.22(1H, dd, J=6.9, 3.0 Hz), 4.07(2H, t, J=7.4 Hz), 2.60(1H, t, J=6.7 Hz), 2.51(1H, dd, J=11.3, 2.0 Hz), 2.29(1H, m), 2.23(3H, s), 2.20(2H, m), 2.10(1H, m), 2.05–1.95 (2H, m), 1.90(1H, d, J=11.9 Hz), 1.77(2H, m), 1.60–1.52(1H, m), 1.48(1H, m), 0.95(3H, t, J=7.4 Hz) MS (EI) m/e: 386(M$^+$)

Compound 17:

Melting point: 210° C. (decomposition) IR (KBr) $v_{max}$ (cm$^{-1}$): 1720, 1643, 1595, 1559, 1506, 1434 $^1$H-NMR (400 MHz; CD$_3$OD) δ(ppm): 4.03(2H, t, J=7.4 Hz), 3.89(1H, brt, J=2.9 Hz), 2.61(1H, brt, J=6.7 Hz), 2.34(2H, brs), 2.20–2.15 (2H, m), 2.10(2H, dd, J=10.8, 2.8 Hz), 1.98(2H, dd, J=10.8, 2.8 Hz), 1.85–1.75 (4H, m), 0.96(3H, t, J=7.4 Hz) MS (EI) m/e: 331(M$^+$+H) HR-MS(FAB) m/e: Calcd. (C$_{17}$H$_{23}$N$_4$O$_3$) 331.1770; Found 331.1758

Reference Example 1

1-(2-Oxopropyl)-8-(3-tricyclo[3.3.1.0$^{3,7}$] nonyl)-3-propylxanthine (Compound C)

Cesium carbonate (3.24 g, 9.95 mmol) and bromoacetone (1.23 ml, 13.3 mmol) were successively added to 35 ml of dimethylformamide solution of 2.20 g (6.63 mmol) of 6-amino-1-propyl-5-(3-tricyclo[3.3.1.0$^{3,7}$]-nonylcarbonylamino) uracil (Japanese Published Unexamined Patent Application No.173889/91) with stirring, followed by stirring at 60° C. for 3.5 hours. After cooling, the reaction solution was poured into 100 ml of water and extracted three times with 30 ml of chloroform. An organic layer was washed with a 0.2M aqueous solution of sodium thiosulfate, water, and then saturated saline, and dried over anhydrous sodium sulfate, and the solvent was distilled off under reduced pressure. The residue was purified by silica gel column chromatography (eluent: 2% methanol/chloroform) to give 1.70 g (yield 66%) of 6-amino-3-(2-oxopropyl)-1-propyl-5-(3-tricyclo[3.3.1.0$^{3,7}$] nonylcarbonyl-amino)uracil (Compound B) as a pale yellow powder.

IR (KBr) $v_{max}$ (cm-1): 1725, 1701, 1637, 1491 $^1$H-NMR (270 MHz; CDCl$_3$) δ(ppm): 7.28(1H, brs), 5.68(2H, brs), 4.74(2H, s), 3.88(2H, t, J=7.4 Hz), 2.74(1H, t, J=7.0 Hz), 2.37(2H, brs), 2.23(3H, s), 2.12–2.08 (2H, m), 1.92–1.55 (10H, m), 1.00(3H, t, J=7.4 Hz) MS (EI) m/e (relative intensity): 388(70, M$^+$), 149(100), 121(90)

A suspension of Compound B (1.70 g, 4.38 mmol) and calcium hydroxide (2.27 g, 30.7 mmol) in water (30 ml) -ethanol (22 ml) was refluxed under heating for 30 minutes. After cooling, the reaction solution was adjusted to pH 2 with concentrated hydrochloric acid, and then extracted three times with chloroform. The extract was washed with saturated saline and dried over anhydrous magnesium sulfate, and the solvent was distilled off under reduced pressure. The obtained crude product was recrystallized from acetone/water to give 874 mg (yield 54%) of Compound C as white plates.

Melting point: 210.8–212.5° C. Elemental analysis: C$_{20}$H$_{26}$N$_4$O$_3$ Calcd.(%): C 64.85, H 7.07, N 15.12 Found (%): C 65.21, H 7.47, N 15.19 IR (KBr) $v_{max}$ (cm$^{-1}$): 1720, 1700, 1655, 1553, 1499 $^1$H-NMR (270 MHz; CDCl$_3$) δ(ppm): 4.83(2H, s), 4.09(2H, t, J=7.5 Hz), 2.74(1H, t, J=6.9 Hz), 2.39(2H, brs), 2.25(3H, s), 2.27–2.20(2H, m), 1.95–1.60(10H, m), 0.96(3H, t, J=7.4 Hz) MS (EI) m/e (relative intensity): 370(100, M$^+$), 327(86)

Reference Example 2

1-(2-Hydroxypropyl)-8-(3-tricyclo[3.3.1.0$^{3,7}$]-nonyl)-3-propylxanthine (Compound D)

Lithium borohydride (102 mg, 4.22 mmol) was added under ice-cooling to 22 ml of a ethanolic solution of 780 mg (2.11 mmol) of Compound C obtained in Reference Example 1, followed by stirring at room temperature for 1.5 hours. The reaction solution was adjusted to pH 3 with 1N hydrochloric acid, and then extracted three times with chloroform. The extract was washed with saturated saline and dried over anhydrous magnesium sulfate, and the solvent was distilled off under reduced pressure. The obtained crude product was recrystallized from acetonitrile to give 440 mg (yield 56%) of Compound D as white prisms.

Melting point: 194.7–196.9° C. Elemental analysis: C$_{20}$H$_{28}$N$_4$O$_3$ Calcd.(%): C 64.49, H 7.58, N 15.04 Found (%): C 64.59, H 7.84, N 15.07 IR (KBr) $v_{max}$ (cm$^{-1}$): 1703, 1655, 1553, 1497 $^1$H-NMR (270 MHz; CDCl$_3$) δ(ppm): 10.84(1H, brs), 4.17–4.06 (5H, m), 3.23(1H, d, J=4.9 Hz), 2.76(1H, t, J=6.9 Hz), 2.41(2H, brs), 2.22–2.18(2H, m), 2.05–1.68 (10H, m), 1.26(3H, d, J=5.6 Hz), 0.97(3H, t, J=7.4 Hz) $^{13}$C-NMR (270 MHz; CD$_3$OD) δ(ppm): 162.4, 156.2, 153.3, 149.8, 108.2, 66.6, 50.7, 49.8, 48.9, 46.9, 46.0, 44.7, 39.0, 35.7, 22.4, 21.1, 11.4 Ms (EI) m/e (relative intensity): 372(12, m$^+$), 354(21), 328(19), 315(100), 279(22)

Industrial Applicability

According to the present invention, there can be provided a novel process for producing xanthine derivatives having adenosine A$_1$ receptor antagonizing activity, and exhibiting diuretic effect, renal-protecting effect, bronchodilatory effect, cerebral function improving effect, etc.

We claim:

1. A process for producing a xanthine derivative, comprising the steps of:

selecting a compound according to formula (I):

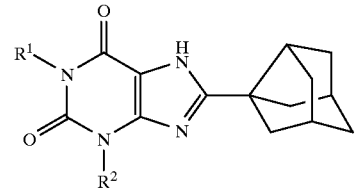

(I)

wherein R$^1$ and R$^2$ are independently hydrogen, or hydroxy-substituted, oxo-substituted, or unsubstituted lower alkyl;

selecting an enzyme source for catalyzing hydroxylation or carbonylation of said compound according to formula (I), wherein said enzyme source is produced by a microorganism selected from the group consisting of a bacterium and a fungus;

admixing said compound according to formula (I) with said enzyme source for catalyzing hydroxylation or carbonylation of said compound according to formula (I) so as to convert said compound according to formula (I) into a compound according to formula (II):

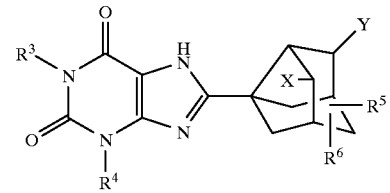

(II)

wherein R$^3$ and R$^4$ are independently hydrogen, or hydroxy-substituted, oxo-substituted, or unsubstituted lower alkyl; R$^5$ and R$^6$ are independently hydrogen, hydroxy, or oxo, with the proviso that R$^5$ and R$^6$ are not simultaneously hydrogen; and X and Y are both hydrogen or are combined with each other to form a single bond; and recovering the compound according to formula (II) produced thereby.

2. A process for producing a xanthine derivative, comprising the steps of:

selecting a compound according to formula (III):

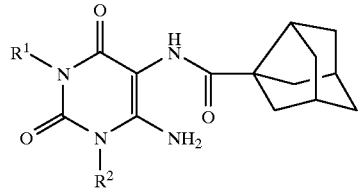

(III)

wherein R$^1$ and R$^2$ are independently hydrogen, or hydroxy-substituted, oxo-substituted, or unsubstituted lower alkyl;

selecting an enzyme source for catalyzing hydroxylation or carbonylation of said compound according to formula (III), wherein said enzyme source is produced by a microorganism selected from the group consisting of a bacterium and a fungus;

admixing said compound according to formula (III) with said enzyme source for catalyzing hydroxylation or carbonylation of said compound according to formula (III) to convert said compound according to formula (III) into a compound according to formula (IV):

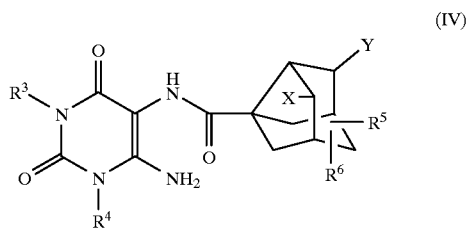

(IV)

wherein $R^3$ and $R^4$ are independently hydrogen, or hydroxy-substituted, oxo-substituted, or unsubstituted lower alkyl; $R^5$ and $R^6$ are independently hydrogen, hydroxy, or oxo, with the proviso that $R^5$ and $R^6$ are not simultaneously hydrogen; and X and Y are both hydrogen or are combined with each other to form a single bond;

conducting hydration on said compound according to formula (IV) to form a closed-ring compound; and recovering the closed-ring compound produced thereby.

3. The process according to any one of claims 1 or 2, wherein $R^1$, $R^2$, $R^3$ and $R^4$ are independently hydroxy-substituted, oxo-substituted, or unsubstituted lower alkyl.

4. The production method according to any one of claims 1 or 2, wherein said microorganism belongs to the genus Absidia, Bacillus, Beauveria, Cunninghamella, Gongronella, or Mucor.

5. The production method according to any one of claims 1 or 2, wherein said microorganism belongs to the species *Absidia ramosa, Bacillus megaterium, Beauveria bassiana, Cunninghamella echinulata* var. *elegans, Gongronella butleri,* or *Mucor hiemalis.*

* * * * *